United States Patent [19]

Leonard et al.

[11] 4,211,086
[45] Jul. 8, 1980

[54] CRYOGENIC BREATHING SYSTEM

[75] Inventors: Rex D. Leonard, Indianapolis, Ind.; Jan Hulstyn, Redondo Beach, Calif.

[73] Assignee: Beatrice Foods Company, Chicago, Ill.

[21] Appl. No.: 19,450

[22] Filed: Mar. 12, 1979

Related U.S. Application Data

[63] Continuation of Ser. No. 840,916, Oct. 11, 1977, abandoned.

[51] Int. Cl.² .............................................. F17C 7/02
[52] U.S. Cl. .......................................... 62/50; 62/55; 128/201.21; 141/5; 222/3
[58] Field of Search .................. 62/50, 52, 55; 141/5, 141/82; 128/142.5, 203, 183, 186, DIG. 27; 222/3

[56] References Cited

U.S. PATENT DOCUMENTS

| 3,199,303 | 8/1965 | Haumann et al. | 62/50 |
| 3,797,262 | 3/1974 | Eigenbrod | 62/50 |
| 3,941,124 | 3/1976 | Rodewald et al. | 62/50 |
| 3,946,572 | 3/1976 | Bragg | 62/50 |
| 4,018,582 | 4/1977 | Hinds et al. | 62/50 |

Primary Examiner—Ronald C. Capossela
Attorney, Agent, or Firm—Jenkins, Coffey, Hyland, Badger & Conard

[57] ABSTRACT

A cryogenic breathing system comprises a storage container and a portable container. Both containers, include outer casings and inner containers having small connected openings at their top and providing an evacuable space between their outer casings and inner containers. Material to inhibit heat transfer through the evacuable space is included in this space between the outer casings and inner containers of both containers. The openings of both containers are closed with gas-tight closures fastened to their outer casings. The gas-tight closures can carry, through the single openings in the containers, means to withdraw oxygen for breathing, liquid level indicating means and a mechanical structure to protect the liquid level indicating means, means to admit or withdraw liquid oxygen from the inner container, and means to admit heat to the inner container, as may be desired.

The portable container is connectable to and fillable from the storage container through the connecting means carried by their respective gas-tight closures by rotating the portable container and engaging the complementary surfaces of the two connecting means and allowing the portable container to return to its vertical position, to open a check valve of the second connecting means, and to lock the portable container to the storage container for filling. Breathing coils on the outer casings of the containers communicate with their inner containers, and flow of gaseous oxygen from the breathing coils can be controlled by an adjustable valve and preset pressure controls of the containers.

19 Claims, 7 Drawing Figures

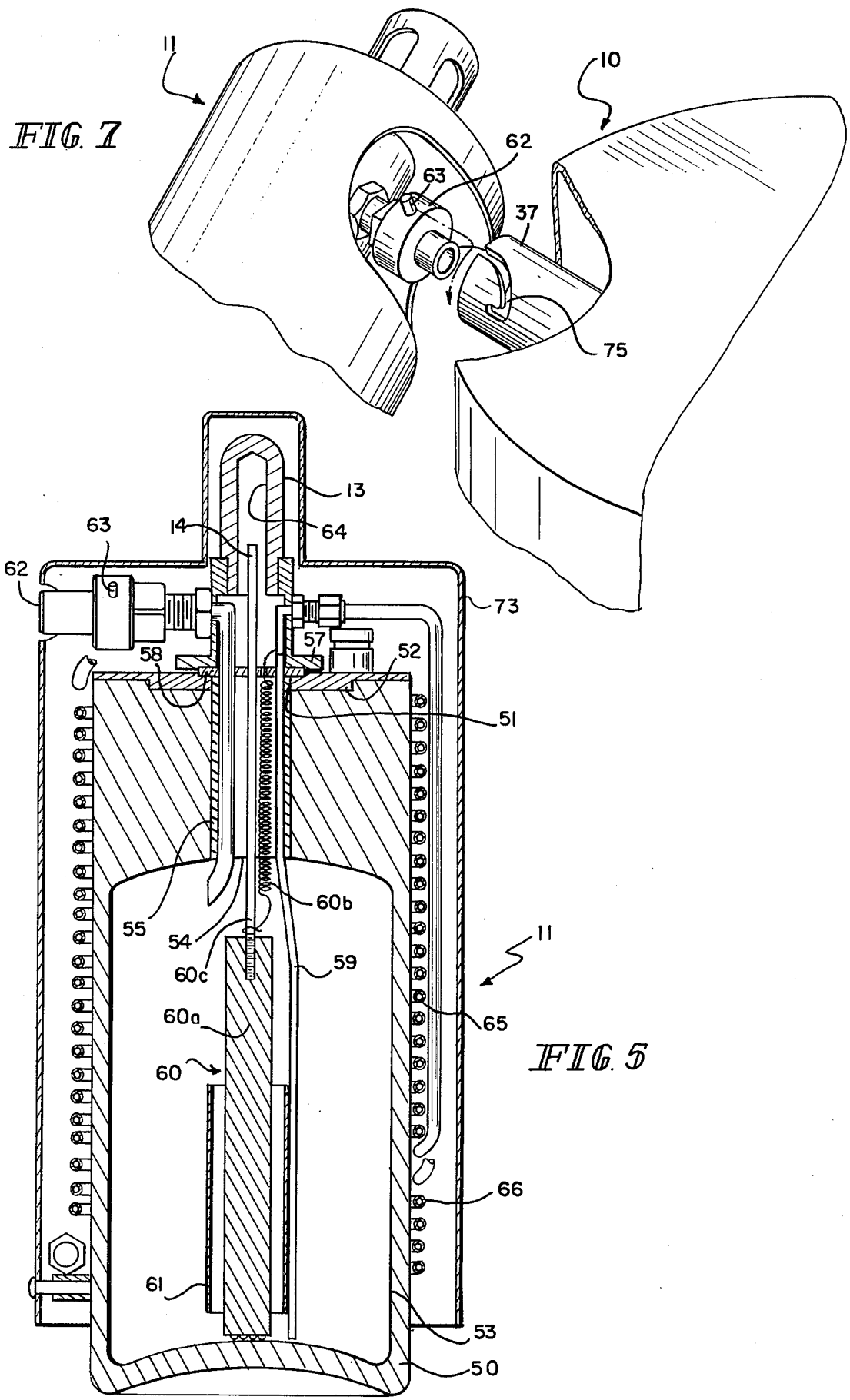

CRYOGENIC BREATHING SYSTEM

This is a continuation of application Ser. No. 840,916 filed Oct. 11, 1977, now abandoned.

This invention relates to a cryogenic system for supplying oxygen for breathing, and more particularly relates to a system including a storage container for liquid oxygen and a portable container for liquid oxygen, the portable container being refillable from the stationary storage container, both containers being able to provide oxygen for breathing.

Many people require supplementary oxygen because of restricted breathing ability due to illness or other physical infirmities. It is desirable that such people remain ambulatory, but the exertion of moving about requires oxygen supplementation of their breathing atmosphere. If the needs of such people for oxygen are satisfied and they can remain ambulatory, they can lead normal lives notwithstanding their infirmities. Physicians are increasingly urging that their patients continue exercise in an effort to lead a normal life for both their physical and mental wellbeing.

Systems exist which provide stationary and portable oxygen supplementation for breathing. An example of such a prior system is disclosed in U.S. Pat. Nos. 3,199,303; 3,797,262; and 3,864,928. Examples of other cryogenic breathing systems are disclosed in U.S. Pat. Nos. 2,943,454; 2,945,354; 2,958,204; 2,964,919; 2,970,452; 3,097,497; 3,117,426; 3,152,589; 3,183,678; 3,186,406; 3,205,670; 3,318,307; 570,481; 3,572,048; 3,707,078.

Many of these prior systems are not adapted to use in the household or to the portability required for ambulatory use. Furthermore, such systems are complex to manufacture and use, and expensive, and beyond the reach of many people who need oxygen supplementation in their daily lives. In addition, prior systems providing a storage container for liquid oxygen and a portable liquid oxygen breathing system required difficult manipulation of the apparatus in order to effect its use.

This invention makes breathing supplementation available to a greater number of people who need it through its less complex structure and the economy of its manufacture and further provides portable breathing supplementation from a system that is more compact and easier to use, thereby reducing the strain on the already limited physical capabilities of the user. The system of this invention provides greater reliability and does not need outside sources of energy for operation, permitting its continued operation in the event of power failure. The system furthermore provides the user with a reliable indication of the availability of supplementary oxygen from the system at all times.

In accordance with the invention, a cryogenic breathing system can include a first cryogenic container for storage of a large quantity of liquid oxygen. Vaporization of the liquid oxygen is minimized by the use of an outer casing and inner container forming an evacuable space therebetween that includes insulating means to inhibit heat transfer between the inner container and ambient atmosphere. The storage container has a flanged opening at the top of its outer casing and is closed by a gas-tight closure attached at the flanged opening. The gas-tight closure carries, within the inner container, a withdrawal tube, and the closure carries, outside of the outer casing, a connecting means in communication with the withdrawal tube and means to control the flow through the withdrawal tube and the connecting means.

In the system, a small cryogenic container is adapted for portability and filling from the storage container. The portable container is likewise adapted to maintain a supply of liquid oxygen, minimizing its evaporation through the use of cryogenic insulating techniques. Accordingly, the portable container has an outer casing and an inner container forming an evacuable space and having, within the evacuable space, insulating means to inhibit the heat transfer from the inner container to ambient atmosphere. The portable container has but one opening at the top which is closed by a gas-tight closure attached to a flange on its outer casing. The gas-tight closure of the portable container carries, within the inner container, a spring-supported liquid level indicating means, a withdrawal tube, and means encircling the spring-supported liquid level indicating means. The closure carries, outside of the outer casing of the portable container, a transparent sight gauge into which the liquid level indicating means extends, a connecting means including a normally closed check valve in communication with the inner container, a warming coil in communication with the withdrawal tube, and means to control the flow of oxygen from the withdrawal tube and warming coil.

The connecting means on the storage container and on the portable container include complementary surfaces to permit the portable container to engage and be supported by the storage container, to open the check valve of the connecting means on the portable container, and the lock the portable container for filling, all by merely tilting the portable container, engaging the connecting means on the two containers, and returning the portable container to a vertical position.

The storage container may also be adapted to provide breathing assistance and include an arrangement to automatically maintain the internal pressure of the container at a preset value. In this respect, the gas-tight closure of the storage container carries, within its inner container, additional withdrawal means, a liquid level indicating means and a coiled tube, and the closure carries, outside of the outer casing, a transparent sight gauge into which the liquid level indicating means extends. Connected with the gas-tight closure and outside of the outer casing are a breathing coil, a vaporizing coil, and a pressure-sensitive valve. The storage container is adapted so that vaporized oxygen is withdrawn from the top of the inner container through the pressure-sensitive valve and the breathing coil for use until such time as the pressure within the container drops below a present value. In the presence of pressure below the preset value, the pressure-sensitive valve closes, and oxygen for use is withdrawn from the container through the vaporizing coil, the coiled tube within the inner container, and the breathing coil in that order. Thus, heat from oxygen which has been warmed in the vaporizing coil outside of the inner container is introduced into the liquid oxygen within the inner container through the walls of the coiled tube, vaporizing the liquid oxygen and thereby increasing the pressure within the container to the preset value. This arrangement results in a supply of gaseous oxygen at a relatively constant preset pressure. No energy other than that available from ambient atmosphere is needed.

By permitting the gas-tight closures to be attached to and supported by the rigid and durable outer casings of the containers, mechanical connection and support of the portable container from the storage container may be easily and reliably made. Furthermore, the gas-tight closures can carry through single small openings in the containers, means to withdraw oxygen for breathing, liquid level indicating means and the necessary mechanical structure to protect the liquid level indicating means, means to admit or withdrawn liquid oxygen from the inner container, and if desired, means to admit heat to the inner container.

In using the system of this invention to fill the portable container, the empty portable container is rotated so that its vertical axis if angularly displaced and pushed so the connecting means on the portable container engages with connecting means on the storage container and complementary mating surfaces of the two connecting means are engaged. The portable container is returned to its vertical position, and the two engaged complementary surfaces of the connecting means pull the portable container toward the stationary container, providing support for the portable container from the stationary storage container, opening the check valve of the portable container, and locking the portable container to the stationary container in a position permitting the portable container to be filled. Vent valves on the portable container and on the storage container are then opened, permitting the vapor pressure in the storage container as a result of vaporization of the liquid oxygen to force liquid oxygen through the connecting means into the portable container. Flow is permitted to continue until such time as the portable container is cooled and is filled with liquid oxygen. An indication of when the portable container is filled is readily determined from the liquid level indicating means at the top of the portable container. When the liquid level indicating means in the portable container indicates that the container is full of liquid oxygen, flow is terminated by closing the vent valves.

The features of the invention are further illustrated in the following drawings in which:

FIG. 5 is a cross-sectional view of a portable container of this invention;

FIG. 7 is a perspective view of a system of this invention being engaged for filling of the inner container.

Figure 1:
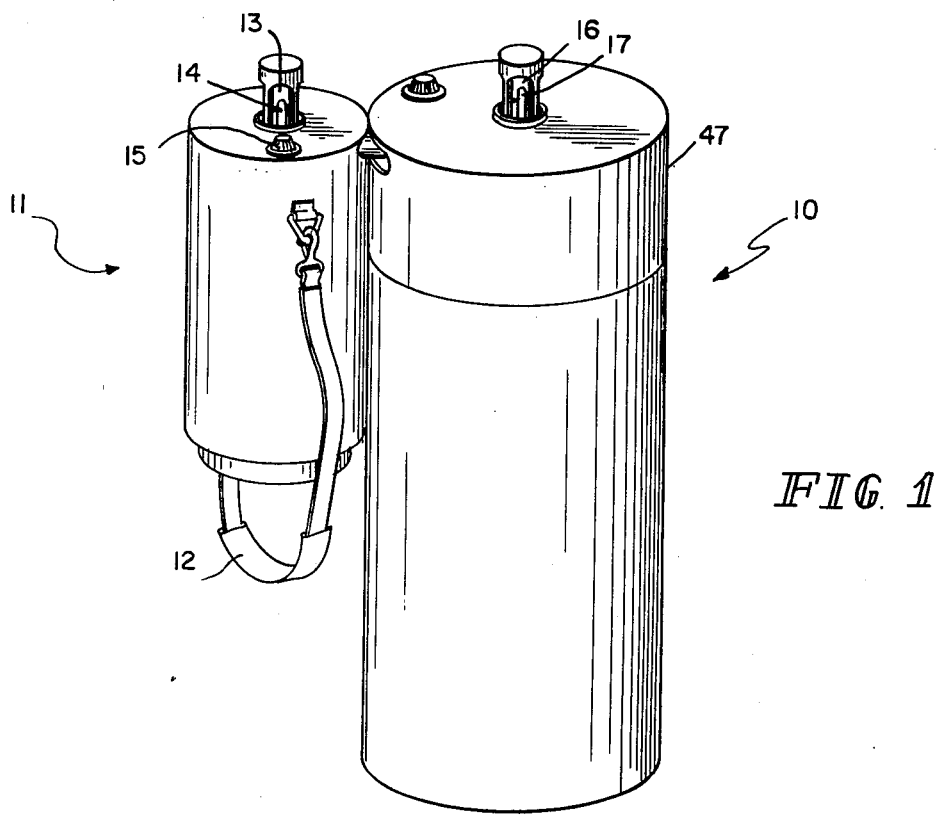
FIG. 1 is a perspective view of a system of this invention showing a portable container supported by a storage container in position to be filled.

A cryogenic breathing system of this invention includes a storage container 10 and a portable container 11. The storage container 11 provides a large supply of liquid oxygen and may be adapted to provide a flow of gaseous oxygen for breathing assistance in the household of a user. Portable container 11 includes a shoulder strap 12 adapted to carry the container 11 over the shoulder of a user. When carried, the portable container of a user provides a flow of oxygen for breathing while the user is moving about in normal activity. The portable container provides at its top a visible indication of the level of liquid oxygen present within the container. This visible indication is provided by means of a sight gauge 13 permitting the user to view a liquid level indicating means 14. An adjustable valve 15 permits the user to adjust the rate of flow of oxygen for his consumption. The storage container 10 likewise provides visible indication of the level of oxygen within the container. This visible indication, like that of the portable container, includes a sight gauge 16 permitting the user to observe a liquid level indicator 17. Where the storage container provides breathing assistance to a user, it includes an adjustable valve 18 to permit the user to control the flow of oxygen for consumption.

As shown in FIG. 1, the portable container 11 may be supported by the portable container 10 for filling, the support and interconnection being accomplished by a connecting means of the portable container 11 and complementary connecting means of the storage container 10 in a manner to be described.

Figure 2:
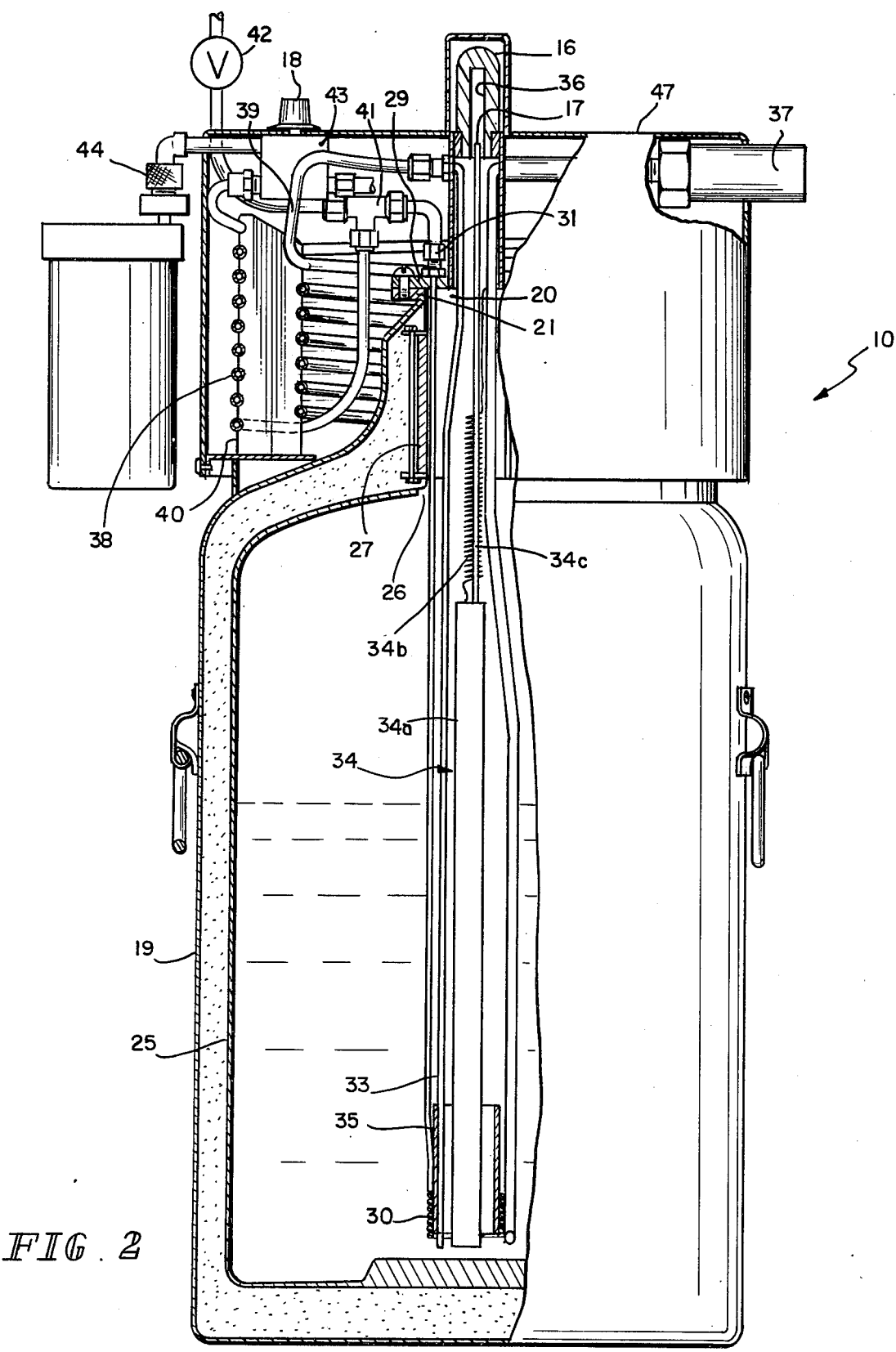
FIG. 2 is a partial cross-sectional view through the center of a storage container of this invention.
Figure 3:
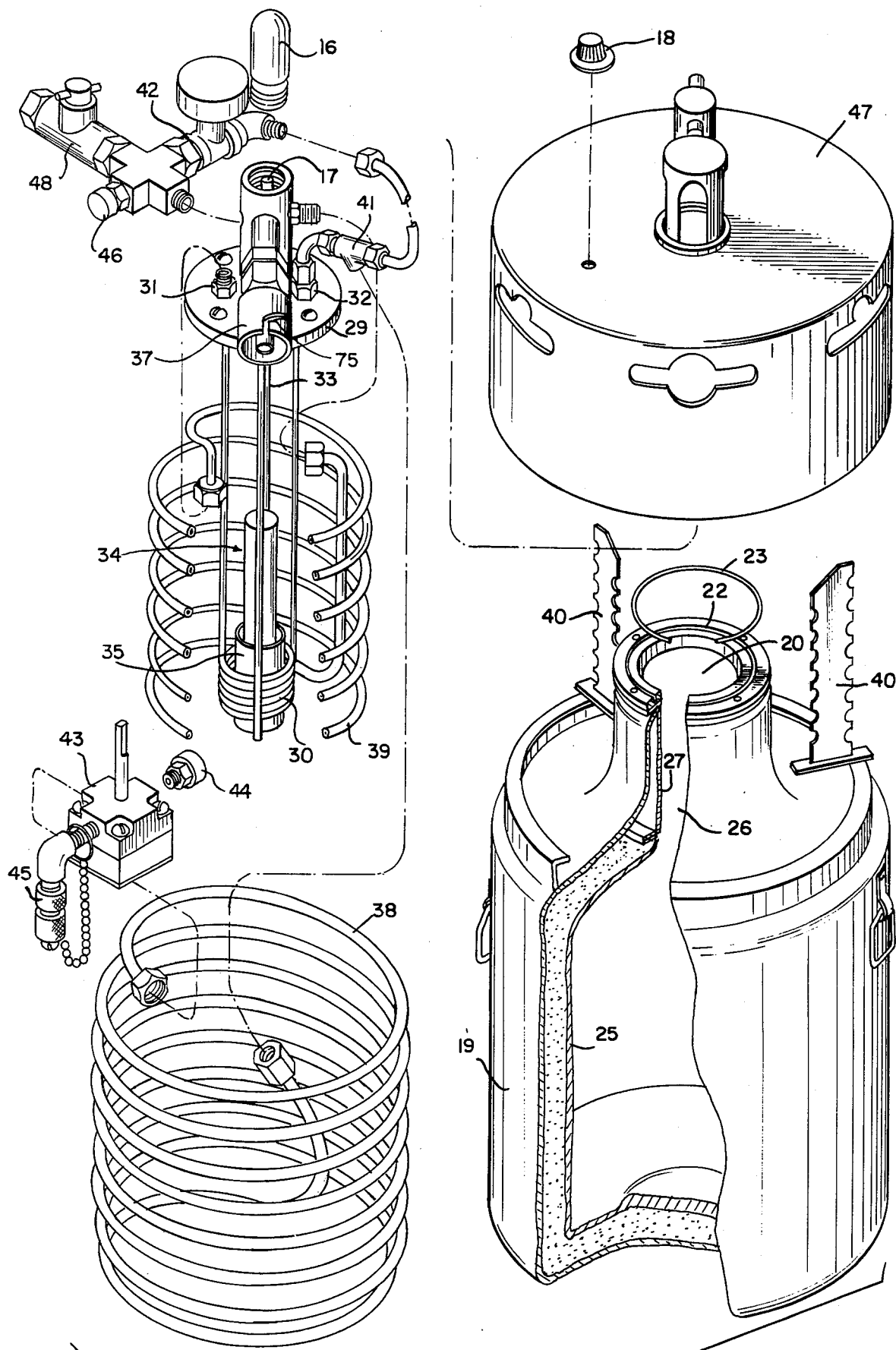
FIG. 3 is a perspective view of a storage container of this invention that is exploded to show its parts and their arrangement.

FIG. 2 and FIG. 3 illustrate the structure of the storage container 10. The storage container 10 includes a rigid outer casing 19 having a small opening 20 at its top encircled by a flange 21 having a channel 22 adapted to receive an O-ring seal 23. The storage container 10 also includes an inner container 25 having a small opening 26 at its top. Openings 20 and 26 of the outer casing and inner container, respectively, are connected together by a gas-tight tubular connection 27 forming an evacuable space between the outer casing and inner container. Tubular connection 27 can be adapted to permit thermal expansion and contraction and other variations of the spacing between the inner container 25 and the outer casing 19. To further inhibit heat transfer between the inner container and the outer case, this evacuable space is filled with multiple layers of thermal insulation including alternate layers of material having poor heat conductivity and layers having high heat reflectivity. Such insulation reduces heat transfer by reducing radiation and conduction of heat through the space between the outer casing and inner container. In addition, zeolite materials are provided in the evacuable space to absorb residual molecules remaining after evacuation of the space as is known in the art. Containers of this construction permit cryogenic fluids, such as liquid oxygen, to be maintained in liquid form for extended periods of time.

As shown in FIGS. 2 and 3, the opening at the top of the storage container is closed by a plate-like closure means 29 which can be fastened to flange 21 by four threaded fasteners. Closure means 29 carries within the inner container a coiled tube 30 which may be connected with tube fittings 31 and 32 on the cosure. Closure 29 also carries a withdrawal tube 33 having its opening adjacent the bottom of the inner container and a spring-supported liquid level indicator 34 adjacent the central axis of the closure means 29. The coiled tube 30 conveniently encircles the liquid level detector means 34 and may be supplemented by a tubular means 35. The closure member 29, upon its assembly to the storage container, carries, within the inner container 25 through the openings 20 and 26, means to indicate the level of liquid within the inner container, means to permit the addition and withdrawal of liquid oxygen from the inner container, and means to provide thermal energy to the inner container, as will be described. At the outside of the storage container, the sight gauge 16 is threadedly connected to the closure means 29, and the top end 17 of the liquid level indicating means 34 extends within a central bore 36 of the sight gauge 16. Also carried by the closure means 29 outside of the outer casing is a connecting means 37 to permit engagement and support of portable container 11 for filling.

The system of this invention provides oxygen for breathing while maintaining the pressure within the storage container and portable container at very low pressure on the order of twenty pounds per square inch above atmospheric pressure. Thus, where the storage container 10 is adapted to provide oxygen for breathing, it includes a breathing coil 38 and a vaporizing coil 39 carried concentrically about closure 29 of the outer casing by a plurality of supports 40.

Figure 4:
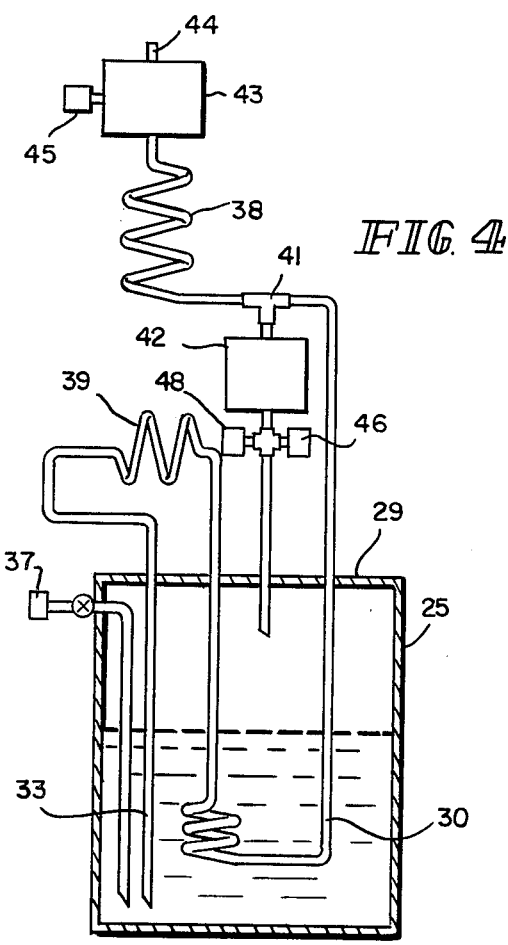
FIG. 4 is a schematic diagram of a system of a storage container of this invention.

As shown in FIG. 4, breathing coil 38 is connected at one end to a fitting 41 and a pressure-sensitive valve 42 that is connected with an opening in the closure 29 and thus with the vaporized oxygen at the top of the inner container 25. The other end of the breathing coil 38 is connected to an adjustable flow control valve 43 (the dial 18 of which is shown in FIG. 1). The valve 43 provides means to control the flow of oxygen from the inner container to the user for consumption by for example, a plurality of orifices of different areas, permitting different rates of oxygen flow at the preset and controlled operating pressure of the system. At the output of valve 43 are fittings 44 to which the user may connect a humidifier and other breathing apparatus.

As shown in FIG. 4, breathing coil 38 is also connected through fitting 41 to one side of the coiled tube 30 within the inner container. The other side of coiled tube 30 is connected to one end of vaporizing coil 39, which is connected at its other end to withdrawal tube 33. When the pressure within the inner container drops below a preset value, on the order of 20 p.s.i. gauge, pressure-sensitive valve 42 closes, blocking the flow of gaseous oxygen from the upper portion of the inner container 25 to the breathing coil 38. The pressure within the inner container 25 then forces liquid oxygen through the withdrawal tube 33 and into vaporizing coil 39 where the heat of the ambient atmosphere vaporizes the liquid oxygen. The gaseous oxygen flows through coiled tube 30 near the bottom of the inner container, and out through fitting 41 to breathing coil 38 for consumption. The heat carried into the inner container 25 by the heated and vaporized oxygen is transmitted through coil 30 to the liquid oxygen within the inner container, thereby vaporizing the liquid oxygen and increasing the pressure within the inner container until the pressure opens valve 42, permitting consumption of oxygen from the gaseous oxygen at the upper portion of inner container 25.

In order to prevent excess pressure from being generated in the breathing coil, a pressure relief valve 45 is provided upon the adjustable control 43. A pressure relief valve 46 is also provided in communication with the upper portion of the inner container to prevent excess pressure from being generated in the inner container in the event of a failure of the tubing, fittings, or valves of the system.

The closure 29 also carries a fitting 37 communicating with the interior of the inner container and including a check valve in order that the storage container may be refilled when the liquid oxygen within its interior is exhausted. Fitting 37 also provides connecting means for filling the portable container 11, with complementary surfaces 75 to engage connecting means of the portable container, as shown in FIG. 7.

The liquid level indicating means 34 includes an aluminum rod 34a (FIG. 2), which is supported from the gas-tight closure 29 by a spring 34b. Attached to the top of the aluminum rod 34a is a stainless rod 34c. The top portion 17 of the rod 34c extends into a central bore 36 in the sight gauge 16. In the presence of liquid oxygen, the aluminum rod 34a is lifted by spring 34b by virtue of the liquid oxygen it displaces and the top portion 17 of rod 34c will thus provide within sight gauge 17 an indication of the level of liquid oxygen within the inner container 25. The means 30 and 35 encircling the liquid level indicating means 34 retain it at about the central axis of the inner container 25 regardless of the attitude of the container 10.

The apparatus at the upper portion of the storage container 10 is protected from contact by a dress cover 47.

As shown in FIG. 5, the portable container 11 of the system is constructed in a manner similar to the storage container. The container itself is comprised of an outer casing 50 having an opening 51 and a flange 52 at its top surrounding the opening 51. It also includes an inner container 53 having an opening 54 at its top. The openings 51 and 54 are connected by a gas-tight tubular connection 55 forming an evacuable space between the inner container 53 and the outer casing 50. This evacuable space is filled with a multiplicity of layers of material having a low thermal conductivity alternating with layers having high heat reflectivity. Such means inhibits the heat transfer between the inner container and the outer casing. In addition to these heat transfer inhibiting means, the interval between the outer casing and the inner container to be evacuated contains zeolite molecular seive materials, as is known in the art, to absorb residual molecules remaining after evacuation, and which have been released from the surfaces of the materials within this interval.

The portable container also includes a plate-like closure 57 attached to the flange at the top of the outer casing of the portable container, for example, by four threaded fasteners. The interval between closure 57 and flange 52 is rendered leak-free by a seal 58 between the flange and the closure. Closure 57 carries within the inner container 53 of the portable container a withdrawal tube 59, a spring-supported level indicator 60, and means 61 encircling the liquid level indicating means 60.

On the exterior of the outer casing, closure 57 carries fluid connecting means 62 including a check valve (not shown) within it. Connecting means 62 includes two surfaces 63, one of which is not shown, complementary to mating surfaces 75 in fitting 37 as shown in FIG. 7. Also carried outside of the outer casing is a transparent sight gauge 13 having a central bore 64 into which the upper portion 14 of the liquid level detector 60 extends.

A breathing coil 65 and a warming coil 66 are carried outside the outer casing 50 of the portable container 11 in coils wrapped concentrically with the outer casing 50.

Figure 6:
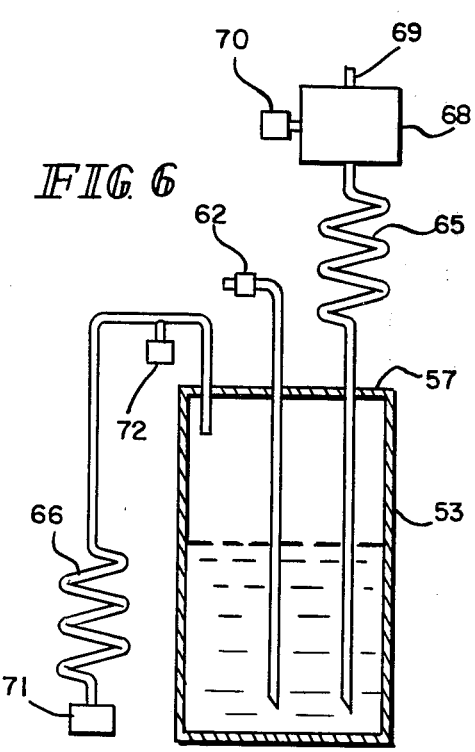
FIG. 6 is a schematic diagram of a system of a portable container of this invention.

As shown in FIG. 6, the breathing coil 65 is connected at one end with an opening in the closure means 57 communicating with the inner container 53. The other end of the breathing coil 65 is connected to an adjustable flow control valve 68 (the adjusting knob of which is shown as 15 of FIG. 1). The adjustable flow control valve 68 provides a plurality of orifices of differing cross sectional areas between the breathing coil and the fitting 69 to which the breathing apparatus of the user is connected, thus providing control of the flow of oxygen to the user. Also connected to the flow control valve 68 is a relief valve 70 to prevent the pressure in the breathing coil from exceeding the preset value of the relief valve.

As shown in FIG. 6, one end of the warming coil 66 is connected to an opening in closure 57 and is in communication with the interior of the inner container. The other end of warming coil 66 is fitted with pressure relief valve 71. This arrangement prevents the pressure within the inner container from exceeding a preset value and delays the escape of liquid oxygen in the event the portable container is inadvertently set down on its side. In addition to the other items carried by plate 57, a vent-to-fill valve 72 is provided which opens the inner container 53 of the portable container to atmosphere during filling operations.

In order to protect the user from inadvertent contact with the portions of the portable container which may be cold and to improve its appearance, the portable container is provided with a dress cover 73, as shown in FIG. 5.

As best seen in FIG. 5, the liquid level indicating means 60 includes an aluminum rod 60a, which is supported from the gas-tight closure 57 by a spring 60b. Attached to the top of the aluminum rod 60a is a stainless rod 60c. The top portion 14 of the rod 60c extends into a central bore 64 in the sight gauge 13. In the presence of liquid oxygen, the aluminum rod 60a is lifted by spring 60b by virtue of the liquid oxygen it displaces, and the top portion 14 of rod 60c will thus provide within sight gauge 13 an indication of the level of liquid oxygen within the inner container 53. The means 61 encircling the liquid level indicating means 60 retains it at about the central axis of the inner container 53 regardless of the attitude of the portable container 11.

In filling the portable container 11 from storage container 10 as shown in FIG. 7, the portable container is rotated so that its vertical axis is at an angle with respect to horizontal and can be rotated so that its vertical axis is at an inclination approximately 45° displaced from the vertical. Connecting means 62 of the portable container is positioned adjacent the connecting means 37 of storage container 10 and the complementary surfaces 63 of the portable container 11 (which is shown to be a pin) and 75 of the storage container 10 (which is shown to be a shaped slot) are positioned for engagement.

As the complementary shapes 63 and 75 are engaged and as the portable container 11 is rotated back to the vertical position, the portable container 11 is pulled toward the storage container 10, drawing fitting 62 into fitting 37 so that container 11 is supported by the storage container 10 and locking the portable container 11 to the storage container 10. The vent-to-fill valve 72 of the portable container (FIG. 6) is then opened using a special tool, and valve 48 on the storage container 10 is also opened, permitting the pressure within the inner container 25 of the storage container to force liquid oxygen through the connecting means 62 and 37 into the inner container 53 of the portable container. Flow is permitted to continue until the liquid level indicating means 14 of the portable container indicates that the portable container 11 is full of liquid oxygen, and valves 48 and 72 are then closed, completing filling of the portable container.

With the portable container 11 full, a user may attach, to fitting 69 of flow control valve 68, a breathing mask and by adjustment of the variable flow control valve 68 obtain a controlled flow of oxygen from the portable container as the user moves about.

Those portions of the system that may be exposed to liquid oxygen must be oxygen compatible. The metallic portions of the apparatus are preferably stainless steel. The transparent sight gauges and dress cover are preferably a material like that sold by the General Electric Company under its trademark LEXAN.

While the description and drawings of this application present a specific preferred embodiment of the invention, different sizes and configurations of the apparatus and method may be used without departing from the scope of my invention as disclosed in the following claims.

I claim:

1. A cryogenic breathing system comprising a first storage container including a first outer casing and a first inner container, the first casing and first container each having a small opening, a first tubular connection between the openings of the first casing and first container, and means between the first casing and first container inhibiting heat transfer therebetween, said storage container providing an evacuable space between its outer casing and its inner container, a first gas-tight closure for said openings fastened to the first outer casing and carrying within the first inner container a first withdrawal tube, the first gas-tight closure carrying outside the first outer casing a first connecting means in communication with the first withdrawal tube and including a first complementary surface, and first means to control flow through the first withdrawal tube and first connecting means, and a second portable container including a second outer casing and a second inner container, the second outer casing and second inner container having a small opening, a second tubular connection between the openings of the second outer casing and second inner container, and further means between the second casing and second inner container inhibiting heat transfer therebetween, said portable container providing an evacuable space between the second outer casing and the second inner container, a second gas-tight closure for said second openings carrying within the second inner container a liquid level indicating means, a withdrawal tube, and means encircling the liquid level indicating means, the second gas-tight closure carrying outside the second outer casing a transparent sight gauge into which the liquid level indicating means extends, a second connecting means including a normally closed check valve in communication with the second inner container and including a second complementary surface adapted to engage the first connecting means of the first storage container, a breathing coil in communication with the second withdrawal tube and a second means to control flow through the second withdrawal tube and breathing coil, said portable container being connectable to and fillable from said storage container through said first and second connecting means by rotating the portable container and engaging the first and second complementary surfaces of the two connecting means and allowing the portable container to return to its vertical position, to open the check valve of the second connecting means, and to lock the second portable container to the first storage container for filling.

2. The cryogenic breathing system of claim 1 wherein the storage container is adapted to provide breathing assistance and said first gas-tight closure carries within the first inner container a coiled tube connected to additional openings in said first closure, an additional liquid level indicating means and an additional withdrawal tube; and said first gas-tight closure carries outside of the first outer casing a transparent sight gauge into which said additional liquid level indicating means extends, a breathing coil, a vaporizing coil, and a pressure-sensitive valve; said breathing coil being connected through the pressure-sensitive valve with the interior of the first inner container and also being connected through an additional closure opening with one end of the coiled tube within the first inner container; one end of the vaporizing coil being connected through another additional closure opening with the other end of the coiled tube within the first inner container and the other end of the vaporizing coil being connected with said additional withdrawal tube; said pressure-sensitive valve maintaning pressure within the first inner container by remaining open to flow from the first inner container directly to the breathing coil in the presence of pressure within the first inner container in excess of a preset pressure and closing to terminate such flow when the pressure of the first inner container drops below the preset pressure so that liquid oxygen flows through said additional withdrawal tube, the vaporizing coil, and the coiled tube within the inner container to the breathing coil, thereby introducing heat into the first inner container to vaporize the liquid oxygen and return the pressure within the first inner container to its preset value.

3. A cryogenic breathing system comprising a storage container for liquid oxygen including an outer casing and an inner container, the casing and container each forming small openings, a gas-tight tubular connection between the openings of the outer casing and the inner container to accommodate thermal and mechanical variations in spacing between the outer casing and the inner container, means between the outer casing and inner container inhibiting heat transfer therebetween, said storage container forming an evacuable space between the outer casing and the inner container,

- a gas-tight closure for the openings of the outer casing and inner container supported by a flange on the outer casing and carrying within the inner container a spring-supported liquid level indicating means, a coiled tube connected to openings in said closure, as support rod, and a withdrawal tube, said coiled tube encircling the liquid level indicating means and being supported by the support rod adjacent the bottom of the inner container,
- said gas-tight closure carrying outside the outer casing a transparent sight gauge into which the liquid level indicating means extends, a vaporizing coil encircling the gas-tight closure and connected at one end with the withdrawal tube and at the other end with the coiled tube within the inner container, a breathing coil encircling the gas-tight closure and connected at one end to the top of the inner container through a pressure-sensitive valve and at the other end to a flow control valve to provide a source of oxygen for breathing, the other end of the coiled tube within the inner container also being connected with said one end of the breathing coil, the pressure-sensitive valve being operable to close the flow of oxygen from the upper portion of the inner container to the breathing coil when the pressure of the inner container drops below a preset value whereby liquid oxygen is drawn from the inner container through the vaporizing coil and the coiled tube within the container to the breathing coil, thereby providing heat into the inner container to increase the inner container pressure to the preset value.

4. A method of filling a portable breathing apparatus with liquid oxygen from the contents of a large storage container comprising rotating the empty portable container so that its vertical axis is angularly displaced from vertical; pushing the portable container to engage connecting means on the portable container with connecting means on the storage container, said two connecting means having complementary mating surfaces and said connecting means on the portable container including a spring-loaded check valve; and returning the portable container to its original position so that the complementary mating surfaces of the two connecting means pull the portable container toward the storage container, mating the two connecting means to support the portable container from the storage container, to open the check valve of the connecting means of the portable container, and to lock the portable container to the storage container; and opening vent valves on the storage container and the portable container, permitting the pressure in the storage container due to the vaporization of liquid oxygen to force the liquid oxygen through the connecting means into the portable container; and closing the vent valves of the portable container and the storage container to terminate the flow of liquid oxygen when the portable container is full.

5. A portable container for liquid oxygen breathing systems comprising an outer casing and an inner container, the outer casing and inner container forming small openings, a gas-tight tubular connection between the openings of the outer casing and inner container formed from a material resistant to the conduction of heat energy, means between the outer casing and inner container inhibiting heat transfer therebetween, said portable container forming an evacuable space between the outer casing and the inner container,

- a metal plate attached to a flange at the opening of the outer casing and forming a gas-tight closure of said openings and carrying within the inner container a spring-supported liquid level indicating means, a withdrawal tube, and means encircling the liquid level indicating means adjacent the bottom of the inner container,
- said plate carrying outside the outer casing a transparent sight gauge into which the liquid level indicating means extends, a breathing coil wrapped about the outer casing and connected at one end with the withdrawal tube and at the other end with an adjustable flow control valve adapted to be connected to a breathing apparatus, a fitting including a normally closed check valve communicating with the inner container, a vaporizing coil wrapped around the outer casing and including a pressure relief valve open to atmosphere, and a manually operable valve to open the inner container to atmospheric pressure and to permit filling of the portable container through said fitting.

6. A cryogenic breathing system comprising
a storage container adapted to maintain a supply of oxygen in liquid state and a portable container adapted to provide a portable supply of liquid oxygen, said storage container and said portable container each including a single opening at their top, first and second closures for the openings of the storage container and portable container respectively, said first and second closures being supported by the structure of the containers and carrying means to interconnect the containers, to support the portable container from the storage container, and to lock the portable container in a supported position from the storage container for filling, said first closure carrying within the storage container a withdrawal tube in communication with said means, and said second closure carrying within the portable container a withdrawal tube, and a liquid oxygen indicating means mechanically actuated by the level of the liquid oxygen within the container and adapted for viewing through a sight gauge, and said second closure means carrying outside of the portable container the sight gauge, a breathing tube in communication with the interior of the portable container to warm oxygen withdrawn therefrom for breathing and an adjustable valve to control the flow of oxygen from the breathing tube.

7. The cryogenic breathing system of claim 6 wherein said first closure carries within the storage container, a liquid level indicating means, a coiled tube connected to openings in said closure, a support rod, and a withdrawal tube, said coiled tube encircling the liquid level indicating means and being supported by the support rod adjacent the bottom of the storage container, and said first closure carries outside the storage container a sight gauge for viewing the liquid level indicating means, a vaporizing coil connected at one end with the withdrawal tube and at the other end with the coiled tube within the storage container, a breathing coil connected at one end through a fitting to the interior of the storage container through a pressure-sensitive valve and at the other end to a flow control valve to provide a source of oxygen for breathing, the other end of the coiled tube within the storage container also being connected through the fitting of the breathing coil, the pressure-sensitive valve being operable to close the flow of oxygen from the upper portion of the storage container to the breathing coil when the pressure of the storage container drops below a preset value whereby liquid oxygen is drawn from the storage container through the vaporizing coil and the coiled tube within the storage container to the breathing coil, thereby providing heat into the storage container to increase the inner container pressure to the preset value.

8. The cryogenic breathing system of claim 7 wherein the vaporizing coil and breathing coil encircle the first closure and are covered by a dress cover at the top of the storage container.

9. The cryogenic breathing system of claim 6 wherein the first closure is a metal plate attached to a flange at the opening of the storage container and forming a gas-tight closure of said opening and carrying within the inner container a spring-supported liquid level indicating means, and means encircling the liquid level indicating means adjacent the bottom of the inner container.

10. The cryogenic breathing system of claim 6 wherein said second closure carries a vaporizing coil wrapped around the outer casing and including a pressure relief valve open to atmosphere, and a manually operable valve to open the inner container to atmospheric pressure and to permit filling of the portable container through said fitting.

11. The cryogenic breathing system of claim 10 wherein the breathing tube is wrapped around the portable container.

12. A cryogenic breathing system comprising a first storage container including a first outer casing and a first inner container, the first casing and first container each having a small opening, a first tubular connection between the openings of the first casing and first container, and means between the first casing and first container inhibiting heat transfer therebetween, said storage container providing an evacuable space between its outer casing and its inner container, a first gas-tight closure for said openings fastened to the first outer casing and carrying within the first inner container a first withdrawal tube, the first gas-tight closure carrying outside the first outer casing a first connecting means in communication with the first withdrawal tube and including a first complementary surface, and first means to control flow through the first withdrawal tube and first connecting means, and a second portable container including a second outer casing and a second inner container, the second outer casing and second inner container having a small opening, a second tubular connection between the openings of the second outer casing and second inner container, and further means between the second casing and second inner container inhibiting heat transfer therebetween, said portable container providing an evacuable space between the second outer casing and the second inner container.

a second gas-tight closure for said second openings carrying within the second inner container a liquid level indicating means, a withdrawal tube, and means protecting the liquid level indicating means, the second gas-tight closure carrying outside the second outer casing a visual presentation of the liquid level indicating means, a second connecting means including a normally closed check valve in communication with the second inner container and including a second complementary surface adapted to engage the first connecting means of the first storage container, a breathing coil in communication with the second withdrawal tube and a second means to control flow through the second withdrawal tube and breathing coil, said portable container being connectable to and fillable from said storage container through said first and second connecting means by rotating the portable container and engaging the first and second complementary surfaces of the two connecting means and counter rotating the portable container to open the check valve of the second connecting means, and to lock the second portable container to the first storage container for filling.

13. A portable container for liquid oxygen breathing systems comprising an outer casing and an inner container, the outer casing and inner container forming small openings, a gas-tight tubular connection between the openings of the outer casing and inner container formed from a material resistant to the conduction of heat energy, means between the outer casing and inner container ihibiting heat transfer therebetween, said portable container forming an evacuable space between the outer casing and the inner container,
- a metal plate attached to a flange at the opening of the outer casing and forming a gas-tight closure of said openings and carrying within the inner container a protected liquid level indicating means and a withdrawal tube,
- said plate carrying outside the outer casing a visual presentation of the liquid level indicating means, a breathing coil wrapped adjacent the outer casing and connected at one end with the withdrawal tube and at the other end with an adjustable flow control valve adapted to be connected to a breathing apparatus, a fitting including a normally closed check valve communicating with the inner container, a vaporizing coil wrapped adjacent the outer casing and including a pressure relief valve open to atmosphere, and a manually operable valve to open the inner container to atmospheric pressure and to permit filling of the portable container through said fitting.

14. A cryogenic breathing system comprising
a storage container adapted to maintain a supply of oxygen in liquid state and a portable container adapted to provide a portable supply of liquid oxygen, said storage container and said portable container each including a single opening at their top,
first and second closures for the openings of the storage container and portable container respectively, said first and second closures being supported by the structure of the containers and carrying means to interconnect the containers, to support the portable container from the storage container, and to lock the portable container in a supported position from the storage container for filling,
said first closure carrying within the storage container a withdrawal tube in communication with said means,
and said second closure carrying within the portable container a withdrawal tube, and a liquid oxygen indicating means actuated by the level of the liquid oxygen within the container and adapted to provide a visual presentation of the level of oxygen within the container, and said second closure means carrying outside of the portable container the visual presentation, a breathing tube in communication with the interior of the portable container to warm oxygen withdrawn therefrom for breathing and an adjustable valve to control the flow of oxygen from the breathing tube.

15. The cryogenic breathing system of claim 14 wherein said first closure carries within the storage container, a liquid level indicating means, a coiled tube connected to openings in said closure, a support rod, and a withdrawal tube, said coiled tube encircling the liquid level indicating means and being supported by the support rod adjacent the bottom of the storage container, and
said first closure carries outside the storage container a visual presentation of the liquid level indicating means, a vaporizing coil connected at one end with the withdrawal tube and at the other end with the coiled tube within the storage container, a breathing coil connected at one end to the interior of the storage container through a pressure-sensitive valve and at the other end to a flow control valve to provide a source of oxygen for breathing, the other end of the coiled tube within the storage container also being connected to the breathing coil, the pressure-sensitive valve being operable to close the flow of gaseous oxygen from the interior of the storage container to the breathing coil when the pressure of the storage container drops below a preset value whereby liquid oxygen is drawn from the storage container through the vaporizing coil and the coiled tube within the storage container to the breathing coil, thereby providing heat into the storage container to increase the inner container pressure to the preset value.

16. The cryogenic breathing system of claim 15 wherein the vaporizing coil and breathing coil encircle the first closure and are covered by a dress cover at the top of the storage container.

17. The cryogenic breathing system of claim 14 wherein the first closure is a metal plate attached to a flange at the opening of the storage container and forming a gas-tight closure of said opening and carrying within the inner container a liquid level indicating means, and means protecting the liquid level indicating means adjacent the bottom of the inner container.

18. The cryogenic breathing system of claim 14 wherein said second closure carries a breathing coil and a vaporizing coil adjacent the outer casing, said vaporizing coil including a pressure relief valve open to atmosphere, and a manually operable valve to open the inner container to atmospheric pressure and to permit filling of the portable container through said fitting.

19. A method of filling a portable breathing apparatus with liquid oxygen from the contents of a large storage container comprising rotating the empty portable container about a generally horizontal axis; pushing the portable container to engage connecting means on the portable container with connecting means on the storage container, said two connecting means having complementary mating surfaces and said connecting means on the portable container including a spring-loaded check valve; and counter rotating the portable container so that the complementary mating surfaces of the two connecting means pull the portable container toward the storage container, mating the two connecting means to support the portable container from the storage container, to open the check valve of the connecting means of the portable container, and to lock the portable container to the storage container; and opening vent valves on the storage container and the portable container, permitting the pressure in the storage container due to the vaporization of liquid oxygen to force the liquid oxygen through the connecting means into the portable container; and closing the vent valves of the portable container and the storage container to terminate the flow of liquid oxygen when the portable container is full.

* * * * *

UNITED STATES PATENT AND TRADEMARK OFFICE
CERTIFICATE OF CORRECTION

PATENT NO. : 4,211,086
DATED : July 8, 1980
INVENTOR(S) : Rex D. Leonard et al.

It is certified that error appears in the above—identified patent and that said Letters Patent is hereby corrected as shown below:

Col. 1, line 31, correct "570,481" to read --3,570,481--.

Col. 2, line 32, delete "the", first occurrence, and insert therefor --to--; line 52, delete "present" and insert therefor --preset--.

Col. 3, line 7, delete "withdrawn" and insert therefor --withdraw--.

Col. 4, line 50, delete "cosure" and insert therefor --closure--; line 56, delete "means" and insert therefor --member--; and line 57, delete "member" and insert therefor --means--.

Col. 5, line 20, after the word "by" insert --,-- (a comma).

Col. 7, line 27, delete "60bby" and insert therefor --60b by--.

UNITED STATES PATENT AND TRADEMARK OFFICE
CERTIFICATE OF CORRECTION

PATENT NO. : 4,211,086
DATED : July 8, 1980
INVENTOR(S) : Rex D. Leonard et al.

It is certified that error appears in the above—identified patent and that said Letters Patent is hereby corrected as shown below:

Col. 9, line 50 (claim 3, line 17), delete "as" and insert therefor --a--.

Col. 12, line 68 (claim 13, line 8), delete "ihibiting" and insert therfor --inhibiting--.

Signed and Sealed this

Second Day of December 1980

[SEAL]

Attest:

Attesting Officer

SIDNEY A. DIAMOND

Commissioner of Patents and Trademarks